(12) United States Patent
Xing et al.

(10) Patent No.: US 11,928,718 B2
(45) Date of Patent: Mar. 12, 2024

(54) METHOD AND SYSTEM FOR LEARNING WATER CONTENT IN FUEL

(71) Applicant: Ford Global Technologies, LLC, Dearborn, MI (US)

(72) Inventors: Yun Xing, Canton, MI (US); John Erik Mikael Hellstrom, Ann Arbor, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 190 days.

(21) Appl. No.: 17/448,670

(22) Filed: Sep. 23, 2021

(65) Prior Publication Data

US 2023/0089626 A1    Mar. 23, 2023

(51) Int. Cl.
*G06Q 30/00* (2023.01)
*B60K 15/03* (2006.01)
*G01N 33/28* (2006.01)
*G06Q 30/0601* (2023.01)
*B60S 5/02* (2006.01)

(52) U.S. Cl.
CPC ......... *G06Q 30/0631* (2013.01); *B60K 15/03* (2013.01); *G01N 33/2847* (2013.01); *B60K 2015/03236* (2013.01); *B60S 5/02* (2013.01)

(58) Field of Classification Search
CPC ............. G06Q 30/06–08; B60K 15/00; G01N 33/2847
See application file for complete search history.

(56) References Cited

U.S. PATENT DOCUMENTS

| 6,974,537 B2 | 12/2005 | Abdelqader | |
| 8,781,673 B2 * | 7/2014 | Nunn | F02D 41/0025 |
| | | | 702/50 |
| 2008/0080682 A1 * | 4/2008 | Ogunwale | G06Q 30/02 |
| | | | 379/93.17 |
| 2008/0167812 A1 * | 7/2008 | Geelen | G01C 21/3641 |
| | | | 701/469 |
| 2008/0319947 A1 * | 12/2008 | Latzina | G06F 16/334 |

FOREIGN PATENT DOCUMENTS

| DE | 102007061125 A1 | 7/2008 |
| WO | 2015000783 A1 | 1/2015 |

OTHER PUBLICATIONS

Xing, Y. et al., "Method and System for Water in Fuel Prognostic Monitor," U.S. Appl. No. 17/448,671, filed Sep. 23, 2021, 27 pages.

* cited by examiner

*Primary Examiner* — Ethan D Civan
(74) *Attorney, Agent, or Firm* — Vincent Mastrogiacomo; McCoy Russell LLP (57) ABSTRACT

A method for recommending fuel filling stations based on water in fuel content is disclosed. In one example, a data structure is generated to house data from a plurality of fuel filling stations. The data structure may include data that is indicative of water in fuel. A recommendation for refilling a fuel tank may be provided according to data that is held in the data structure.

14 Claims, 7 Drawing Sheets

METHOD AND SYSTEM FOR LEARNING WATER CONTENT IN FUEL

BACKGROUND/SUMMARY

A vehicle may include a water separator to remove water from fuel. The water may enter fuel that is pumped from a filling station via condensation within fuel tanks or via seepage of water into the fuel tanks. Fuel from some filling stations may include more water than fuel from other filling stations because some filling stations may refill their fuel tanks less often, thereby permitting a greater chance for condensation to form in the fuel tanks. Water in the diesel fuel may cause reduced engine performance, high pressure fuel pump degradation, and fuel injector degradation. As such, it may be desirable to reduce exposing the high pressure fuel pump and fuel injectors to mixtures of fuel and water. One way to reduce a possibility of delivering water to an engine is to fill a vehicle's fuel tank with as little water as may be possible. However, a vehicle operator may have no insight as to which fuel stations supply fuel that has lower water content.

The inventors herein have recognized the above-mentioned disadvantages and have developed a method for operating a vehicle, comprising: displaying a list comprised of one or more fuel refilling stations based on an indication of a content of water in fuel provided by each of the one or more fuel refilling stations.

By displaying a list comprised of one or more fuel refilling stations based on an indication of content of water in fuel, it may be possible to provide the technical result of informing a vehicle operator which fuel source provides a more desirable fuel. The more desirable fuel may contain less water than fuels that are provided via other filling stations. In this way, a vehicle's driver or operator may make a more informed decision regarding where to buy fuel.

The present description may provide several advantages. For example, the approach may help to reduce a possibility of engine and fuel system degradation. Further, the approach may provide information to a vehicle operator so that the vehicle operator may make a more informed decision regarding where to purchase fuel. In addition, the approach may be implemented with existing hardware so as to reduce system cost.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
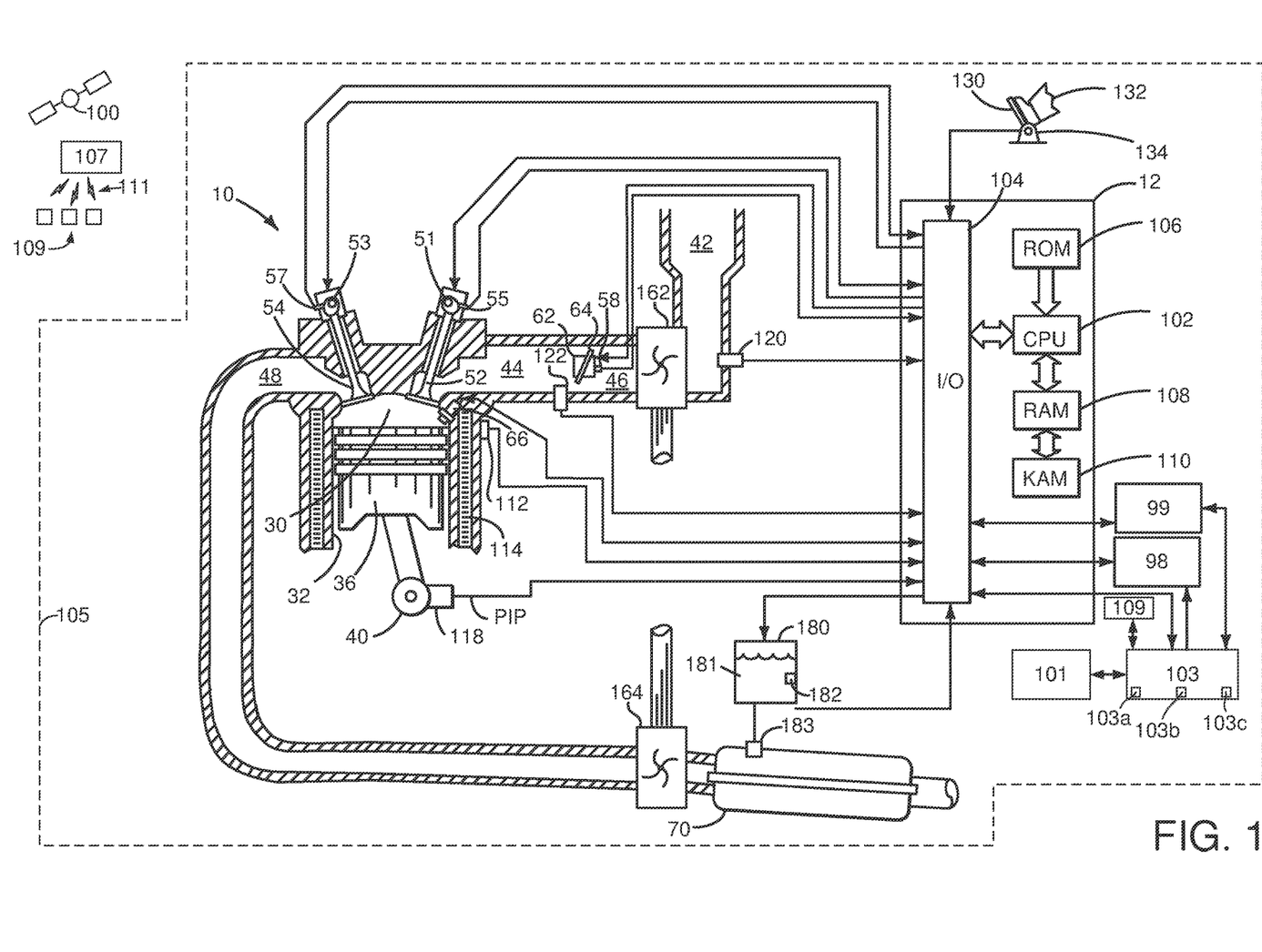
FIG. 1 shows a schematic depiction of an engine.
Figure 2:
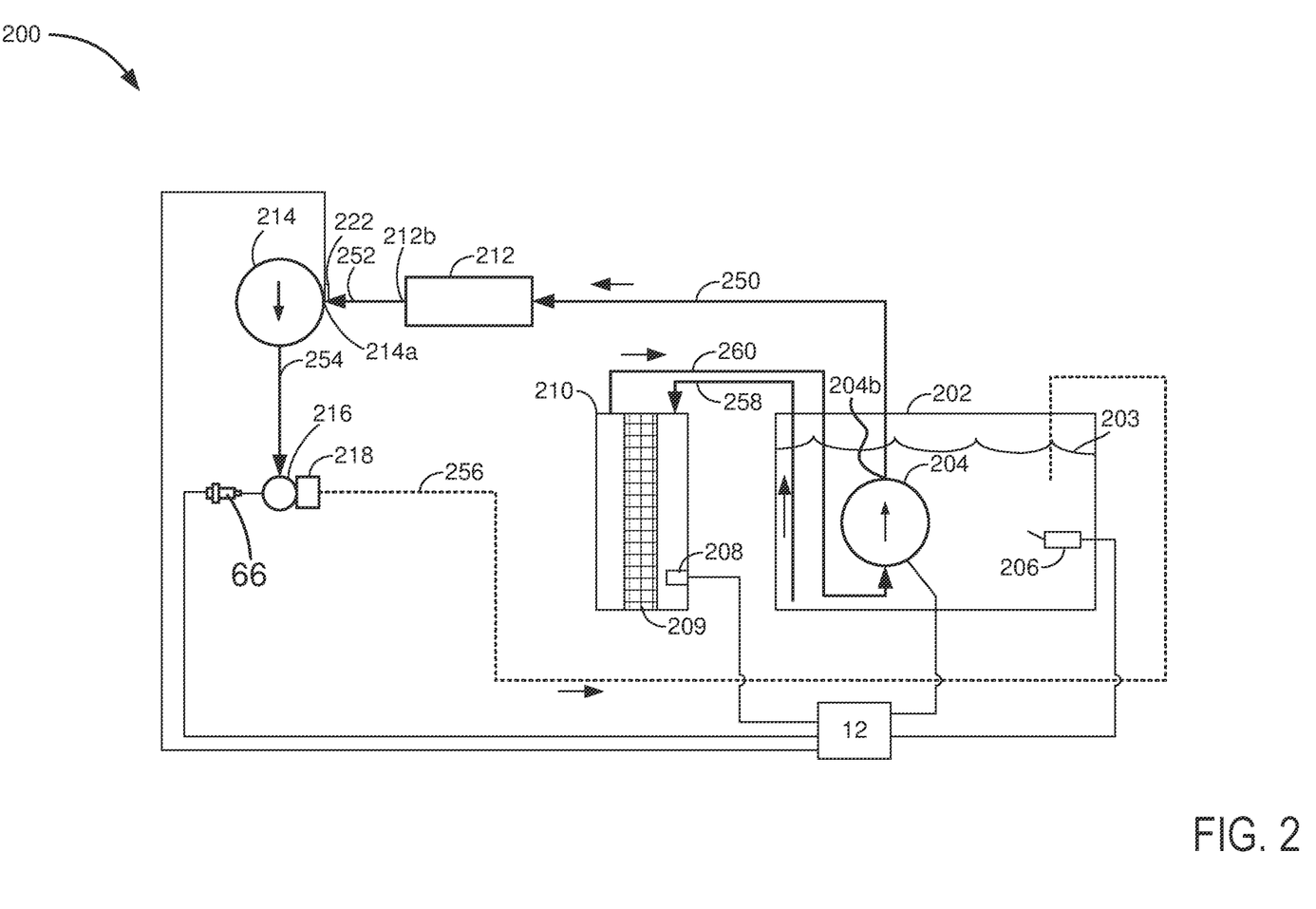
FIG. 2 shows a schematic depiction of a fuel system for the engine of FIG. 1.
Figure 4:
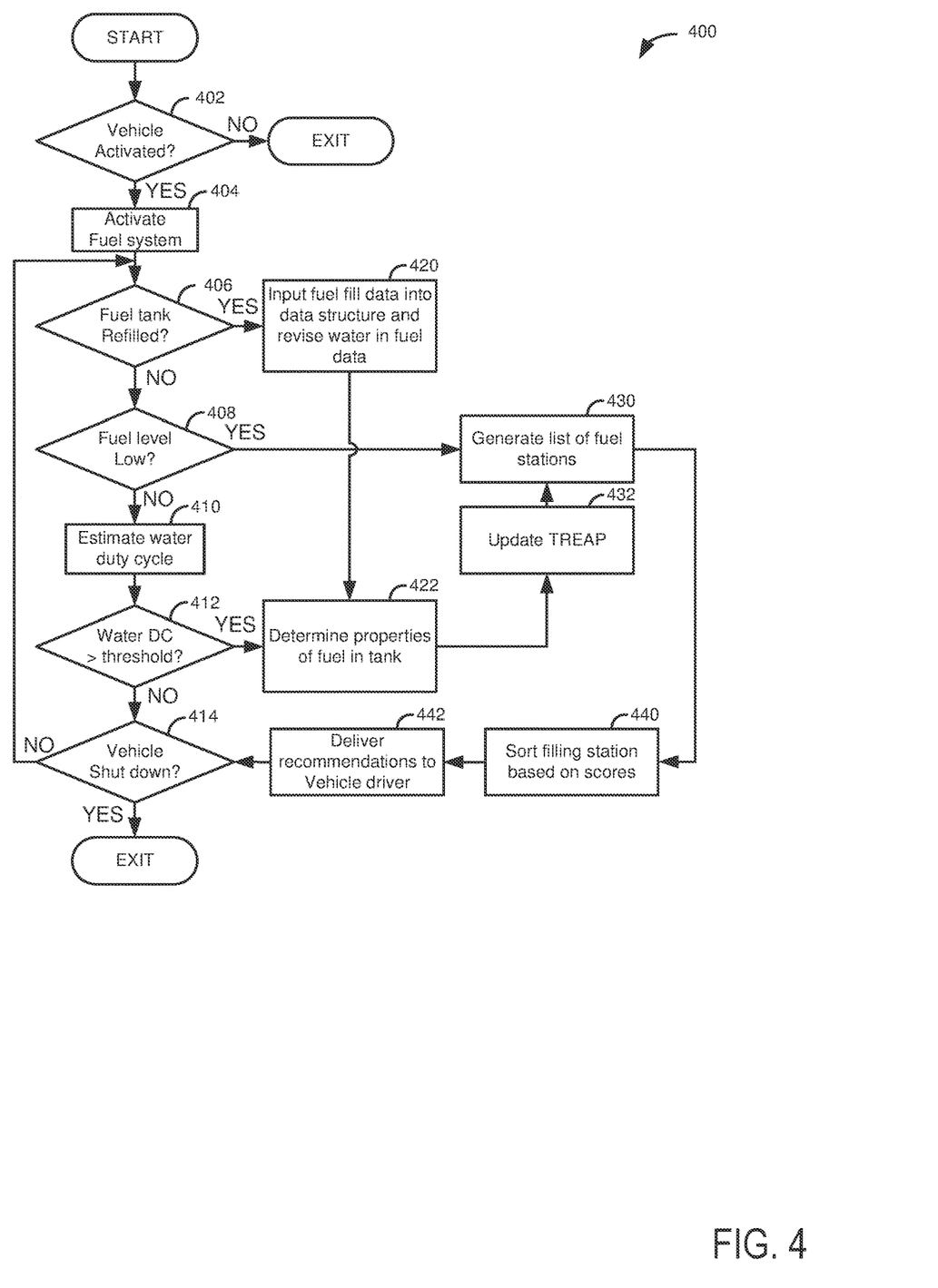
FIG. 4 shows an example method for recommending a fuel station.
Figure 5:
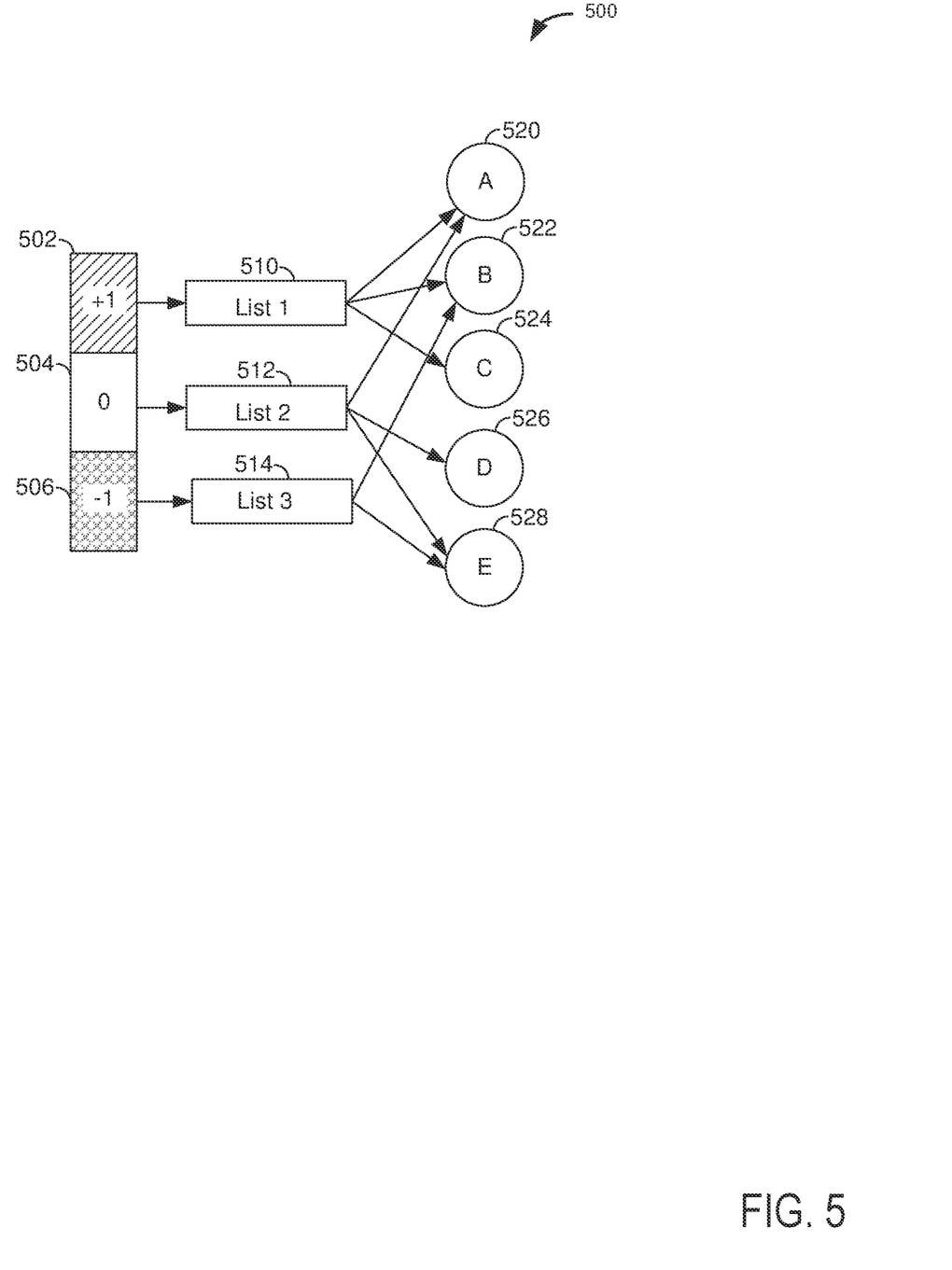
FIG. 5 shows an example for fuel refilling station scoring.
Figure 6:
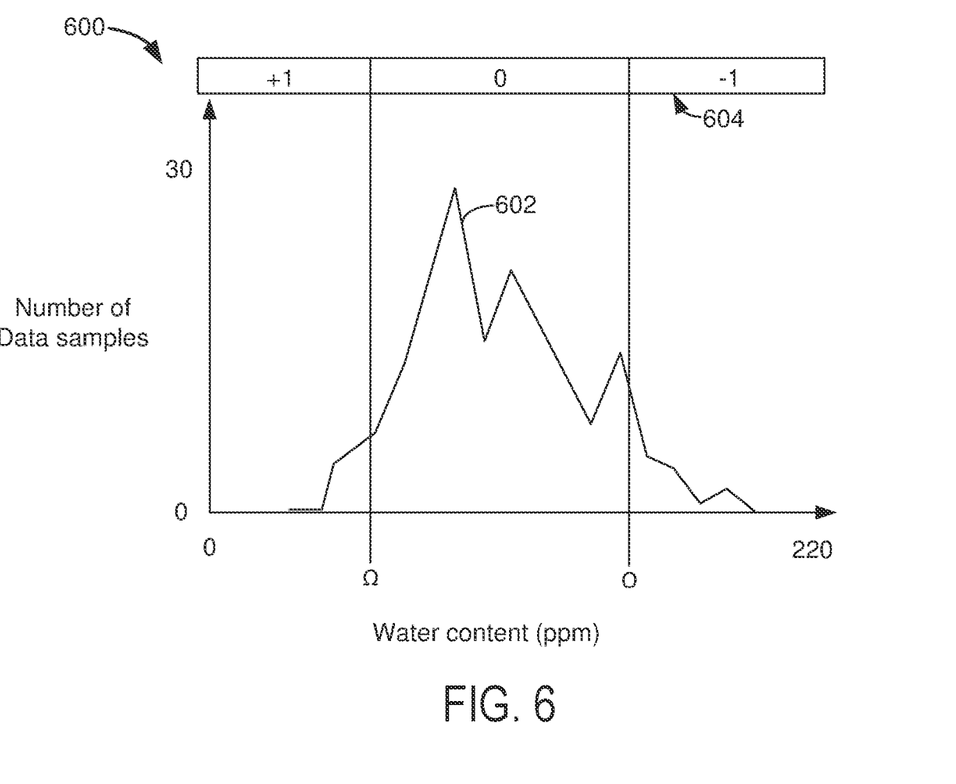
FIG. 6 shows an example water in fuel distribution and scoring values for fuel refilling stations.
Figure 7:
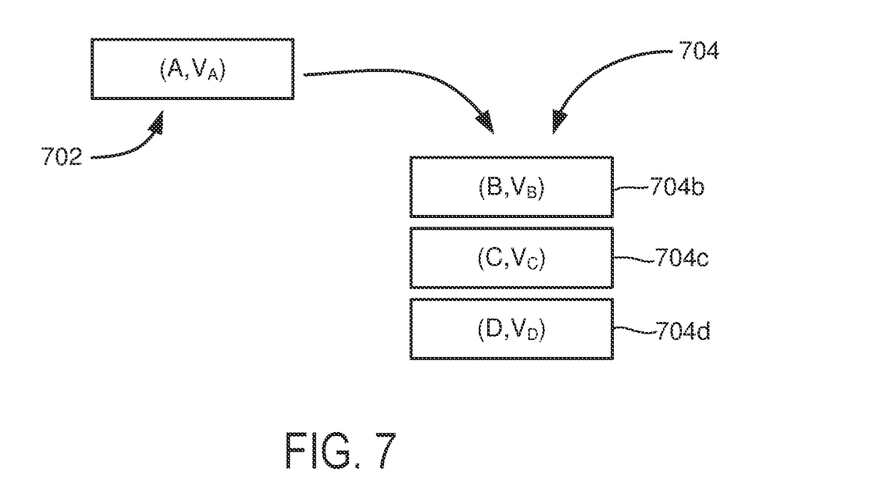
FIG. 7 shows an example data stack for fuel refilling.
Figure 8:
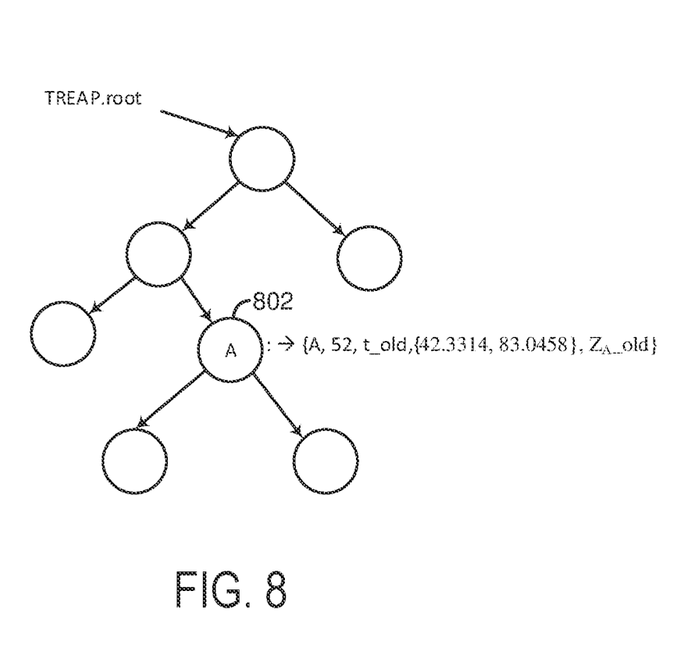
FIG. 8 shows an example TREAP.

The present description is related to delivering recommendations for refilling a fuel tank according to detection of water in fuel. The fuel may be supplied to a boosted direct injection compression ignition engine as shown in FIG. 1. The fuel may be input to a fuel system as shown in FIG. 2. A water in fuel distribution for the fuel may be of the form shown in FIG. 3. A method for making recommendations for refilling a fuel tank is shown in FIG. 4. The method of FIG. 4 may search fuel refilling data via a TREAP as shown in FIG. 5. The method may score fuel and fuel filling stations according to the water in fuel distribution plot shown in FIG. 6. The fuel refilling data may be placed in a data stack as shown in FIG. 7 and data from the data stack may be used to generate a TREAP as shown in FIG. 8.

Referring to FIG. 1, internal combustion engine 10, comprising a plurality of cylinders, one cylinder of which is shown in FIG. 1, is controlled by electronic engine controller 12. Engine 10 includes combustion chamber 30 and cylinder walls 32 with piston 36 positioned therein and connected to crankshaft 40. Combustion chamber 30 is shown communicating with intake manifold 44 and exhaust manifold 48 via respective intake valve 52 and exhaust valve 54. Each intake and exhaust valve may be operated by an intake cam 51 and an exhaust cam 53. The position of intake cam 51 may be determined by intake cam sensor 55. The position of exhaust cam 53 may be determined by exhaust cam sensor 57.

Fuel injector 66 is shown positioned to inject fuel directly into cylinder 30, which is known to those skilled in the art as direct injection. Fuel injector 66 delivers liquid fuel in proportion to the pulse width of a signal from controller 12. Fuel is delivered to fuel injector 66 by a fuel system (not shown) including a fuel tank, fuel pump, fuel rail (not shown). Fuel pressure delivered by the fuel system may be adjusted by varying a position valve regulating flow to a fuel pump (not shown). In addition, a metering valve may be located in or near the fuel rail for closed loop fuel control.

Intake manifold 44 is shown communicating with optional electronic throttle 62 which adjusts a position of throttle plate 64 to control air flow from intake boost chamber 46. Compressor 162 draws air from air intake 42 to supply boost chamber 46. Exhaust gases spin turbine 164 which is coupled to compressor 162.

Combustion is initiated in combustion chamber 30 when fuel automatically ignites as piston approaches top-dead-center compression stroke. In some examples, a universal Exhaust Gas Oxygen (UEGO) sensor (not shown) may be coupled to exhaust manifold 48 upstream of emissions device 70. In other examples, the UEGO sensor may be located downstream of one or more exhaust after treatment devices. Further, in some examples, the UEGO sensor may be replaced by a NOx sensor.

Emissions device 70 can include a particulate filter and catalyst bricks, in one example. In another example, multiple emission control devices, each with multiple bricks, can be used. Emissions device 70 can include an oxidation catalyst in one example. In other examples, the emissions device may include a lean NOx trap or a SCR.

Diesel exhaust fluid (DEF) 181 may be comprised of water and urea. DEF may be stored in reservoir 180 that includes a level sensor 182. The DEF may be injected to the emissions device 70 via injector 183 to reduce NOx into nitrogen and water. DEF may be refilled via a tube or pipe that may be located near the diesel fuel fill tube.

Controller 12 is shown in FIG. 1 as a conventional microcomputer including: microprocessor unit 102, input/output ports 104, read-only memory (e.g., non-transitory memory) 106, random access memory 108, keep alive memory 110, and a conventional data bus. Controller 12 is shown receiving various signals from sensors coupled to engine 10, in addition to those signals previously discussed, including: engine coolant temperature (ECT) from temperature sensor 112 coupled to cooling sleeve 114; a position sensor 134 coupled to an accelerator pedal 130 for sensing accelerator position adjusted by foot 132; a measurement of engine manifold pressure (MAP) from pressure sensor 122 coupled to intake manifold 44; an engine position sensor from a Hall effect sensor 118 sensing crankshaft 40 position; a measurement of air mass entering the engine from sensor 120 (e.g., a hot wire air flow meter); and a measurement of throttle position from sensor 58. Barometric pressure may also be sensed (sensor not shown) for processing by controller 12. In a preferred aspect of the present description, engine position sensor 118 produces a predetermined number of equally spaced pulses every revolution of the crankshaft from which engine speed (RPM) can be determined.

Controller 12 may also receive data from and send data to infotainment controller 103. Infotainment controller 103 may receive powertrain data such as water in fuel data, fuel level, fuel pressure, and fuel system actuator operating states from controller 12. The methods and routines described herein may be performed via infotainment controller 103, controller 12, or a distributed between infotainment controller 103 and controller 12. Infotainment controller 103 includes a controller 103a, read-only memory 103b, and random access memory 103c. The methods and instructions described herein may be stored as executable instructions stored in non-transitory memory (106) of controller 12, non-transitory memory (103b) of infotainment controller 103, or in a combination of controller 12 and infotainment controller 103.

Infotainment controller 103 may receive global positioning system (GPS) data from GPS receiver 101. GPS receiver 101 may receive time stamped data from GPS satellite 100 that allows GPS receiver 101 to determine a location of vehicle 105. The location of vehicle 105 may be used to determine a location of a fuel refilling station. In addition, a location of a fuel refilling station may be determined via an infotainment controller 103. Data and information from controller 12 and infotainment controller 103 may be displayed via human/machine interface 99. Human/machine interface may be a liquid crystal display, touch screen, or other input/output device. Controller 12 may also receive instructions from an autonomous driver 98 to steer and propel a vehicle to a desired location. Autonomous driver 98 may also receive a geographical destination from infotainment controller 103. Infotainment controller 103 may provide navigational directions, present vehicle locations, destinations, music, video, and other services to vehicle occupants via human/machine interface 99. Vehicle data including water in fuel data, TREAP data, and fuel station scoring data may be transmitted from vehicle transceiver 109 to a remote cloud server 107 via satellite 100 or via a cellular (over the air) communication system 111. Cellular communication system may also distribute water in fuel data and TREAP data to a plurality of other vehicles 109 so that the other vehicles may locate fuel stations according to water in fuel data as determined by the controllers of vehicle 105.

In some embodiments, the engine may be coupled to an electric motor/battery system in a hybrid vehicle. The hybrid vehicle may have a parallel configuration, series configuration, or variation or combinations thereof.

During operation, each cylinder within engine 10 typically undergoes a four stroke cycle: the cycle includes the intake stroke, compression stroke, expansion stroke, and exhaust stroke. During the intake stroke, generally, the exhaust valve 54 closes and intake valve 52 opens. Air is introduced into combustion chamber 30 via intake manifold 44, and piston 36 moves to the bottom of the cylinder so as to increase the volume within combustion chamber 30. The position at which piston 36 is near the bottom of the cylinder and at the end of its stroke (e.g. when combustion chamber 30 is at its largest volume) is typically referred to by those of skill in the art as bottom dead center (BDC). During the compression stroke, intake valve 52 and exhaust valve 54 are closed. Piston 36 moves toward the cylinder head so as to compress the air within combustion chamber 30. The point at which piston 36 is at the end of its stroke and closest to the cylinder head (e.g. when combustion chamber 30 is at its smallest volume) is typically referred to by those of skill in the art as top dead center (TDC). In a process hereinafter referred to as injection, fuel is introduced into the combustion chamber. In some examples, fuel may be injected to a cylinder a plurality of times during a single cylinder cycle. In a process hereinafter referred to as ignition, the injected fuel is ignited by compression ignition or by known ignition means such as spark plug (not shown), resulting in combustion. During the expansion stroke, the expanding gases push piston 36 back to BDC. Crankshaft 40 converts piston movement into a rotational torque of the rotary shaft. Finally, during the exhaust stroke, the exhaust valve 54 opens to release the combusted air-fuel mixture to exhaust manifold 48 and the piston returns to TDC. Note that the above is described merely as an example, and that intake and exhaust valve opening and/or closing timings may vary, such as to provide positive or negative valve overlap, late intake valve closing, or various other examples. Further, in some examples a two-stroke cycle may be used rather than a four-stroke cycle.

Referring now to FIG. 2, a detailed view of fuel system 200 for the engine of FIG. 1 is shown. Fuel system 200 includes a fuel tank 202 for storing liquid fuel 203. Fuel 203 may be drawn from fuel tank 202 via conduit or pipe 258 into water separator 210. Water separator 210 includes a water in fuel sensor 208 and a water reservoir 209. Fuel that passes through the water separator 210 may flow to a low pressure fuel pump 204 via conduit or pipe 260. Low pressure fuel pump 204 delivers fuel to a filter 212 from outlet 204a of low pressure fuel pump 204. Fuel exits filter 212 and flows to high pressure pump via conduit 252 and fuel pressure may be measured at an inlet of high pressure fuel pump 214a via pressure sensor 222. Alternatively, pressure sensor 222 may be positioned anywhere along conduit 250 or conduit 252, including at outlet 204b of low pressure fuel pump 204 or at the outlet 212b of fuel filter 212. High pressure fuel pump 214 delivers fuel to fuel rail 216 via conduit 254. Fuel rail 216 includes a pressure sensor and a regulator 218. Fuel may be delivered from fuel rail 216 to engine 10 via fuel injector 66. Regulator 218 may return fuel to fuel tank 202 via conduit or pipe 256 when fuel pressure exceeds a threshold level. A level of fuel in fuel tank 202 may be provided by fuel level sensor 206. The arrows along conduits 258, 260, 250, 252, and 254 indicate the direction of fuel flow from fuel tank 202 to low pressure fuel pump 204 and to high pressure fuel pump 214. Thus, high pressure fuel pump 214 is positioned downstream of low pressure fuel pump 204 according to the direction of fuel flow. Controller 12 may activate sensors shown in FIG. 2 and receive data from sensors shown in FIG. 2.

Thus, the system of FIGS. 1 and 2 provides for a vehicle system, comprising: a fuel tank; a water separator including a water in fuel sensor; and a controller including executable instructions stored in non-transitory memory that cause the controller to generate a data structure that includes data for a plurality of fuel filling stations and data for an amount of fuel received from each of the plurality of fuel filling stations, and instructions to display a list comprised of one or more fuel refilling stations based on an indication of a content of water in fuel provided by each of the one or more fuel refilling stations, the content of water in fuel provided by each of the one or more fuel refilling stations based on data included in the data structure. The vehicle system further comprises additional instructions to estimate the content of water in fuel. The vehicle system further comprises additional instructions to generate scores for each of the one or more fuel refilling stations. The vehicle system includes where the scores are based on the content of water in fuel. The vehicle system further comprises additional instructions to generate a binary search tree. The vehicle system includes where displaying the list includes sorting the one or more fuel refilling stations based on scores of each of the one or more fuel refilling stations. The vehicle system includes where the scores of each of the one or more fuel refilling stations are based on the content of water in fuel. The vehicle system includes where the content of water in fuel is based on output of the water in fuel sensor.

Figure 3:
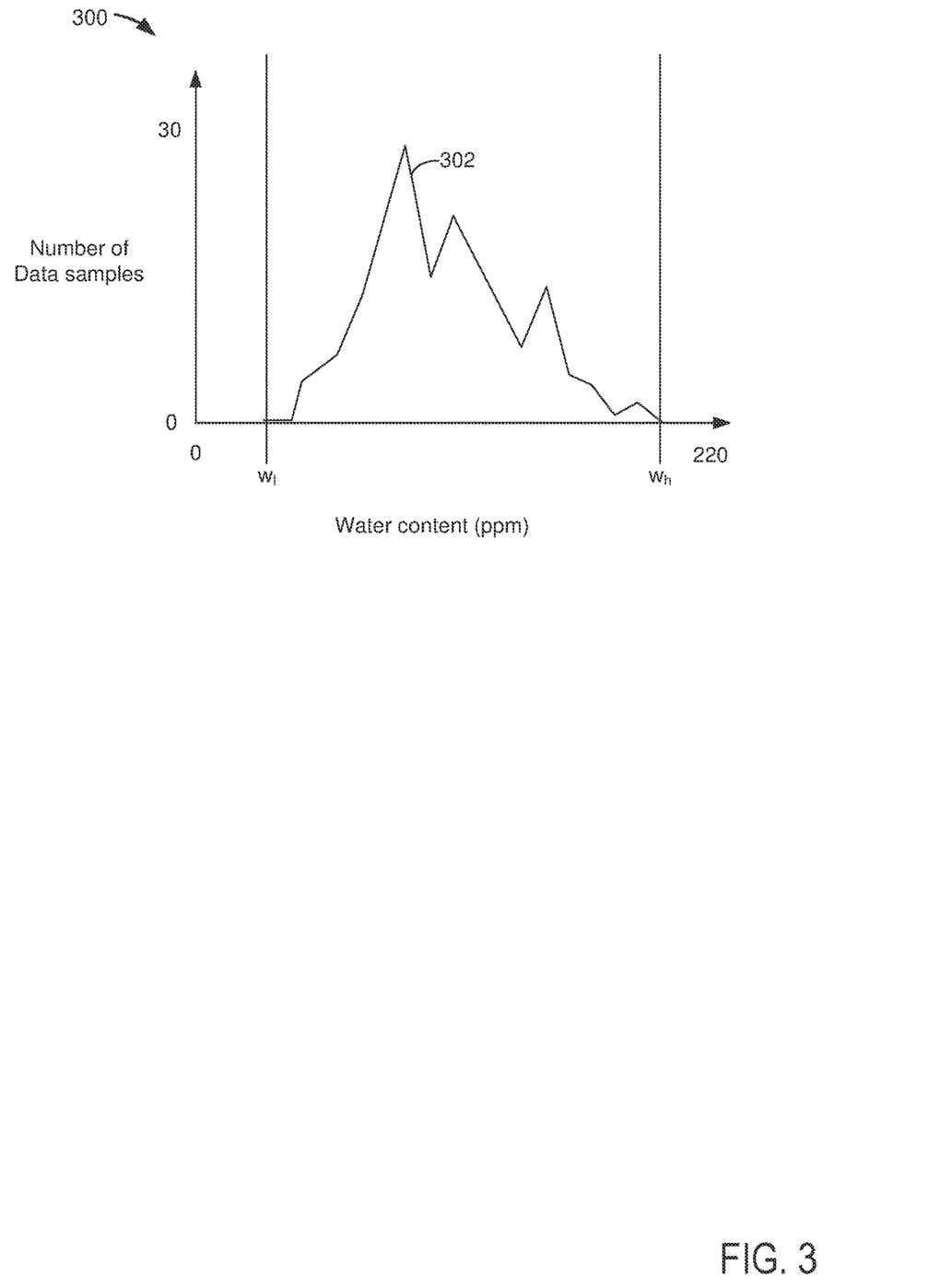
FIG. 3 is a plot of an example distribution for water content in diesel fuel.

Turning now to FIG. 3, a plot of an example distribution of water in diesel fuel is shown. Plot 300 includes a vertical axis that represents an actual number of data samples taken for water in fuel. The actual total number of data samples taken for water in fuel increases in the direction from the horizontal axis to the vertical axis arrow. The horizontal axis represents water content in fuel and the water content in the fuel increases in the direction of the horizontal axis arrow. Curve 302 represents water content in fuel. The lower boundary of water in fuel is indicated by the vertical line $w_l$ and the upper boundary of water in fuel is indicated by the vertical line $w_h$. It may be observed that curve 302 exhibits a shape that is similar to a normal distribution.

Referring now to FIG. 4, a flowchart of an example method for recommending a fuel filling station based on detection of water in fuel is shown. The method of FIG. 4 may be incorporated into and may cooperate with the system of FIGS. 1-2. Further, at least portions of the method of FIG. 4 may be incorporated as executable instructions stored in non-transitory memory of one or more controllers described herein while other portions of the method may be performed via the one or more controllers transforming operating states of devices and actuators in the physical world.

At 402, method 400 determines if the vehicle that includes the engine and fuel system of FIG. 1 is activated. Method 400 may determine that the vehicle is activated based on a position of a key switch, a push button input, a proximity of a key fob, a state of a variable in controller memory, or other known way of activating a vehicle. If method 400 judges that the vehicle is activated, the answer is yes and method 400 proceeds to 404. Otherwise, the answer is no and method 400 proceeds to exit.

At 404, method 400 activates the vehicle's fuel system. Activating the vehicle's fuel system may include activating and/or providing power to one or more fuel pumps in the fuel system. Method 400 may also open and/or close valves to activate the vehicle's fuel system. Method 400 proceeds to 406.

At 406, method 400 judges whether or not a fluid has been added to the vehicle's fuel tank. The fluid is preferably fuel, but it may be possible to add other fluids to the fuel tank. If so, the answer is yes and method 400 proceeds to 420. Otherwise, the answer is no and method 400 proceeds to 408. In one example, method 400 may determine if the fuel tank has been refilled according to the following equation:

$$h_n > h_0 + \varepsilon \qquad (1)$$

where $h_n$ is the present level output via a fuel level sensor, $h_0$ is a saved fuel level from a most recent time that the vehicle was deactivated, and $\varepsilon$ is a threshold offset value.

At 420, method 400 inputs fuel refilling data into a data structure and revises water in fuel data. In one example, method 400 may determine the volume of fuel that has been most recently added to the vehicle's fuel tank via the following equation:

$$V_A = \{f(h_n - h_0)\}_A \qquad (2)$$

where $V_A$ is a volume of fuel attributed to a particular fuel refilling station, f is a function that returns a volume of fuel, $h_n$ and $h_0$ are as previously mentioned and A is encoded data that identifies a fuel refilling station's GPS location. The fuel refilling data (e.g., identity or location of fuel refilling station, volume of fuel added to fuel tank, etc.) may be incorporated into a stack of data as shown in FIG. 7. Specifically as shown in FIG. 7, data from a most recent fuel refilling event (e.g., when fuel was added to the fuel tank) 702 may be added to a stack 704 of data that may be comprised of fuel refilling data from a plurality of prior fuel refilling events 704b-704d. The stack S may be generated via the following instructions (1) and comments for the instructions are bracketed by //:

```
struct refilldata{            // name a structure refilldata
int stationkey; // station identifier is an integer type
double fillamount             // refill fuel amount is a double type
}      // end of structure definition
refilldata.stationkey=A           // identification key of fuel station A
refilldata.fillamount=V_A            // most recent amount of fuel added at station A
S.top=S+1     // adjust stack pointer
S[S.top]=refilldata           // push new refilldata item to stack
```

Method 400 may also determine an amount of water that may be introduced to the vehicles fuel tank via the following equation:

$$\{f(h_n-h_0)\cdot w_l\}_i < \{\text{water added}\}_i < \{f(h_n-h_0)\cdot w_h\}_i \quad (3)$$

where f is a function that returns an amount of fuel given arguments $h_n$ and $h_0$, $h_n$ is a fuel level after a fuel fill, $h_0$ is a fuel level before the most recent fuel fill, water added is an amount of water that is added to the fuel tank due to the fuel refill, $w_l$ is the lower boundary of water content in the fuel, $w_h$ is the upper boundary of water content in the fuel, i is a fuel refill event number, and $h_n$ and $h_0$ are as previously described. A lower boundary and an upper boundary of water in the water reservoir may be determined via the following equations:

$$\text{lower boundary} = \Sigma_i \{f(h_n-h_0)\cdot w_l\}_i \quad (4)$$

$$\text{upper boundary} = \Sigma_i \{f(h_n-h_0)\cdot w_h\}_i \quad (5)$$

where lower boundary is a lower boundary water level in the water reservoir amount, upper boundary is an upper boundary water level in the water reservoir, and the other variables are as previously mentioned. Method 400 proceeds to 422.

At 408, method 400 judges if the fuel level in the fuel tank is low. In one example, if the amount of fuel in the fuel tank as indicated via a fuel level sensor is less than a threshold level, the answer is yes and method 400 proceeds to 430. Otherwise, the answer is no and method 400 proceeds to 410.

At 410, method 400 estimates a water duty cycle value. In one example, method 400 estimates the water duty cycle value as described in U.S. Pat. No. 8,781,673, which is hereby fully incorporated for all intents and purposes. For example, the duty cycle may be determined via the following equation:

$$\text{Duty Cycle} = \frac{\text{water sum}(1) + \text{water sum}(2) + \ldots + \text{water sum}(y)}{\text{bin size}(n) \cdot \text{num bins}(y)} \quad (6)$$

where Duty Cycle is the duty cycle value, water sum (1) is a sum of outputs of a water in fuel sensor for a first bin (e.g., group of memory locations) of water in fuel samples that includes n samples, water sum (2) is a sum of outputs of the water in fuel sensor for a second bin of water in fuel samples that includes n samples, bin size (n) is the total number of water in fuel sensor samples in each bin, and num bins (y) is the total number of bins y. For example, when an output data sample measurement received from the water in fuel sensor indicates that prongs of the second are submerged in water, the cumulative data sum for a bin may increase by a value of one. After a $n^{th}$ water in fuel data output sample is collected, the cumulative sum may be stored in the water sum variable for a particular bin and the bin count number may be increased. A next working data bin may then receive n output samples from the water in fuel sensor. A second stored water sum may then be stored and the bin counter may be increased by one. The collecting and processing of water in fuel sensor output data may be repeated until the bin counter reaches a predetermined value y. The duty cycle calculation represents a percentage of data sample water in fuel measurements that indicate that the prongs of the water in fuel sensor are submerged in water. One of the bins of data may be replaced with newer output data from the water in fuel sensor after a new water sum datum for that bin is available. Method 400 proceeds to 412.

At 412, method 400 judges if the water duty cycle value determined at 410 is greater than a threshold. If so, the answer is yes and method 400 proceeds to 422. Otherwise, the answer is no and method 400 proceeds to 414.

At 414, method 400 judges if the vehicle is to be shut down. Method 400 may judge that the vehicle is to be shut down if the vehicle operator leaves the vicinity of the vehicle, removed a vehicle key, or presses a stop/start button. If method 400 judges that the vehicle is to be shut down, the answer is yes and method 400 stops combustion in the engine and proceeds to exit. Otherwise, the answer is no and method 400 returns to 406.

At 422, method 400 determines properties of fuel that is in the fuel tank. In particular, method 400 determines the water content in the fuel. If the water duty cycle as determined via equation 6 is greater than a threshold dcc, the duty cycle corresponding to the minimum detectable level of water in fuel lp that is detectable by the water in fuel sensor, and lp is between lower and upper bounds, the water content may be determined via the following equation:

$$\delta = \frac{l_p}{\text{total fuel filled}} \quad (7)$$

where $\delta$ is the diesel fuel water content, $l_p$ is the amount of water that is in the water reservoir, and total fuel filled in the fuel tank is given via the following equation:

$$\text{total fuel filled} = \Sigma_i \{f(h_n-h_0)\} \quad (8)$$

where total fuel filled is the amount of fuel that is added to the fuel tank during a series of refills, f is a function that returns a fuel amount based on the present fuel level $h_n$ and the fuel level before the most recent refill $h_0$. The total fuel filled equation may be implemented via the following instructions (2):

```
total_fuel_filled = 0; // initialize the variable total fuel
while stack S is not empty { // loop condition to continue executing instructions
var_pop = Pop(S); // pop up stack datum item
total_fuel_filled += var_pop.fill_amount; // compute total fuel filled
fill_at_this_gas_station (var_pop.station_key)+=var_pop.fill_amount; }//compute
fuel filled at each station
```

Method 400 may also determine a portion of fuel that is refilled each time the vehicle is refueled via the following instructions (3):

for (i=1:n){

$$w(i) = \frac{\text{fill\_at\_this\_fuel\_station}}{\text{total\_filled\_fuel}};\}$$

where i is a variable representing a particular fuel filling station and n is the total number of fuel filling stations.

Method 400 may also score or rank fuel that is delivered by a particular fuel filling station. In one example, method 400 may apply a scoring/ranking system as shown in FIG. 6. In particular, FIG. 6 shows a plot 600 of water in fuel distribution that is subdivided into three ranges. The vertical axis represents an actual number of data samples taken for water in fuel. The horizontal axis represents the water content in fuel. Trace 602 represents the water content in fuel. The first range is for water contents that are less than a predetermined lower threshold Ω. The second range is for water contents that are greater than the lower threshold Ω and less than an upper water content threshold O.

If a fuel filling station supplies fuel with a water content that is lower than some value Ω, the fuel supplied by the fuel station may be assigned a score value of "+1" ("preferred"). If the fuel filling station supplies fuel with a water content that is greater than an upper threshold value O, the fuel supplied by the fuel station may be assigned a score of "−1" ("disfavor"). If a fuel refilling station supplies fuel with a water content that is greater than the lower threshold Ω and less than the upper threshold O, the fuel supplied by the fuel filling station may be assigned a score of "0" ("neutral"). Ranking block 604 indicates such a scoring approach relative to the water in fuel content levels. The following instructions may be applied to score and store fuel refilling stations to a controller data structure:

```
If water content < Ω
    Z = 1              // Z is assigned score = 1
else if water content > O
    Z = −1             // Z is assigned score = −1
else
    Z = 0              // Z is assigned score = 0
```

The scores for individual fuel refilling stations may be determined based on the proportions from instructions (3) according to the following equation:

$$Z_i = Z \cdot w(i) \tag{9}$$

where $Z_i$ is a score for fuel refilling station i, Z is the score value, and w is fuel portion refilled for fuel refilling station i. The following a data structure may be generated via the following instructions (4) after the scores of $Z_i$ have been obtained:

```
struct fuelstation { // declaration, data structure for fuel filling station
int key; // filling station identifier is integer type
int priority; // an integer value as priority for this filling station
time_t time; // refilling time at this filling station
double position[2]; // latitude and longitude for this filling station
double score; // calculated score for this filling station (equation 9)
};
```

In the fuelstation data structure, the variable "priority" is a random number chosen independently for each fuel filling station and time is the timestamp. For example, for a fuel refilling station "A," the assembled data items may be generated via the following instructions (5):
   fuelstation.key=A
   fuelstation.prirority=52
   fuelstation.time=Thu Sep 15 21:18:23 2016
   fuelstation.position={42.3314, 83.0458}
   fuelstation.score=0.3

Thus, the properties of the fuel may be linked with a particular fuel refilling and the fuel properties may be placed in a data structure to facilitate searching. Method 400 proceeds to 432.

At 432, method 400 builds and/or updates a randomized binary search tree (TREAP) for scored fuel refilling stations. The TREAP may be built based on a key and a priority to organize fuel refilling station data, as provided in fuelstation structure for example. Once fuel refilling station "A" is assigned a score "$Z_A$" via equation (9), the TREAP is searched to check if there is a "node" for fuel refilling station "A". A fuel refilling station "A" may be a structure in the TREAP, such as shown in FIG. 8. The TREAP root node is indicated as TREAP.root in FIG. 8. The node for fuel filling station "A" is indicated at 802 and the node for filling station "A" contains data including the key A, priority=52, time of fuel refill t_old, latitude 42.3314, longitude 83.0458, and prior fuel station score $Z_{A\_}$ old. The score of the fuel refilling station may be updated according to the following equation (10) by taking the decay effect of the old score into consideration:

$$Z_A = Z_A + Z_{A\_}\text{old} \cdot (1-r)^{\lambda \cdot (t-t\_old)} \tag{10}$$

where r is an adjustable decay rate and λ is an adjustable scaling factor, t is present time, t_old is a timestamp for when node "A" was last updated, $Z_{A\_}$old is the score for the fuel refilling station the time node "A" was updated, and $Z_A$ is the score for the fuel refilling station for the present fuel refill.

Data for fuel refilling station A in the TREAP may be updated with score "$Z_A$" from equation (10) and time "t" for the present fuel filling event. However, if the search in the TREAP finds no match of filling station "A," then a node for fuel refilling station A with data from instructions (5) may be inserted into this TREAP via the following instructions (6):

```
TREAP-SEARCH(TREAP, A) // search filling station "A" in TREAP
if TREAP == NIL or A == TREAP.key // empty TREAP or A is found in the TREAP
return TREAP // return to TREAP root
if A < TREAP.key     // branch to left sub TREAP
return TREAP-SEARCH(TREAP.left, A) // recursively call the function on sub TREAP
rooted at TREAP.left
else return TREAP-SEARCH(TREAP. right, A) // recursively call the function on sub
TREAP rooted at TREAP.right
if TREAP == NIL      // If A is not found in the TREAP
TREAP-INSERT(TREAP, A) // insert node "A" at current location
else
update TREAP.time and TREAP.score according to equations (10) (11)
```

The following is an illustration for the previously described scoring updating algorithm. Assume the following three lists are obtained from different times:

List 1: [{'A':$w_{1A}$,'B':$w_{1B}$,'C':$w_{1C}$},{'water content':$\delta_1$, $\delta_1 < \Omega$}] @time t1

List 2: [{'A':$w_{2A}$,'D':$w_{2D}$,'E':$w_{2E}$},{'water content':$\delta_2$, $\Omega < \delta_2 < 0$}] @time t2

List 3: [{'B':$w_{3B}$,'E':$w_{3E}$},{'water content':$\delta_3$, $\delta_3 > 0$}] @time t3

According to the score scale shown on FIG. 6, List 1 scores "1," List 2 scores "0," and List 3 scores "−1". The individual fuel refiling station scores may be calculated as:

Score of filling station A: $S_A = w_{1A} \cdot 1 + w_{2A} \cdot 0 \cdot (1-r)^{\lambda \cdot (t1-t2)}$ Score of filling station B: $S_B = w_{1B} \cdot 1 + w_{3B} \cdot (-1) \cdot (1-r)^{\lambda \cdot (t1-t3)}$ Score of filling station C: $S_C = w_{1C} \cdot 1$ Score of filling station D: $S_D = w_{2D} \cdot (-1)$ Score of filling station E: $S_E = w_{2E} \cdot 0 + w_{3E} \cdot (-1) \cdot (1-r)^{\lambda \cdot (t2-t3)}$ where $S_A$ is the updated score for filling station A, $S_B$ is the updated score for filling station B, $S_C$ is the updated score for filling station C, $S_D$ is the updated score for filling station D, $S_E$ is the updated score for filling station E, $w_{1A}$ is proportion of fuel filled in filling station A at time t1, $w_{2A}$ is proportion of fuel filled in filling station A at time t2, $w_{1B}$ is proportion of fuel filled in filling station B at time t1, $w_{3B}$ is proportion of fuel filled in filling station B at time t3, $w_{1C}$ is proportion of fuel filled in filling station C at time t1, $w_{2D}$ is the proportion of fuel filled in filling station D at time t2, $w_{2E}$ is the proportion of fuel filled in filling station E at time t2, $w_{3E}$ is the proportion of fuel filled in filling station E at time t3, r is an adjustable decay rate and $\lambda$ is an adjustable scaling factor, and t1, t2, t3 are respective filling times.

When the fuel level sensor indicates that vehicle fuel level is low, a traversal operation may be performed on the previously mentioned TREAP, and the distance between a TREAP node and a current location (based on GPS info) may be calculated via the following instructions (7):

```
INODER-TREAP-WALK(TREAP) // algorithm to generate list of filling stations
if TREAP != NIL   // entry condition, make sure TREAP is not empty
   INODER-TREAP-WALK(TREAP.left)   // traverse left sub TREAP
   Calculate distance d between TREAP.position and current location
      if d < ∈ (a calibratable threshold value)
         push {TREAP.key, TREAP.score} to a list list_stations_nearby //
         push station key and station score of a TREAP node to an external list
      INODER-TREAP-WALK(TREAP.right) // traverse right sub TREAP
```

Method 400 proceeds to 430 after the TREAP is updated with scoring for the water in fuel data from the most recent fuel filling event.

In some examples, method 400 may transmit fuel station scores and/or receive updates of fuel station scores from a remote cloud server so that a more complete TREAP may be generated by the vehicle and so that other vehicles have the benefit of water in fuel data from the present vehicle.

At 430, method 400 generates a list of nearby fuel filling stations and their associated scores for water in fuel. The list may be generated by instructions (7). Method 400 proceeds to 440.

At 440, method 400 sorts the list of fuel refilling stations based on scores of water in fuel for the fuel refilling stations. Method 400 proceeds to 442.

At 442, method 400 delivers a list of recommended fuel refilling stations to the vehicle's human or autonomous driver. In one example, method 400 may present the list via a human/machine interface. If the vehicle includes an autonomous driver, method 400 may command the autonomous driver to proceed to the nearest fuel refilling station with the highest score. Method 400 proceeds to 414.

In this way, water in fuel may be a basis for scoring fuel refilling stations so that fuels with lower water content may be supplied to the vehicle. The lower water content may reduce engine component degradation and improve vehicle economy.

Thus, the method of FIG. 4 provides for a method for operating a vehicle, comprising: displaying a list comprised of one or more fuel refilling stations based on an indication of a content of water in fuel provided by each of the plurality of fuel refilling stations. The method includes where each of the one or more of fuel refilling stations is a position identified fuel refilling station. The method includes where the indication of content of water is based on an amount of water in a reservoir. The method further comprises generating a scoring system from the indication of content of water in fuel. The method includes where the scoring system includes numerical values that indicate water content in fuel. The method includes where the displaying the list includes displaying the list according to fuel refilling station scores. The method includes where the fuel refilling station scores are based on the water content in fuel.

The method of FIG. 4 also provides for a method for operating a vehicle, comprising: generating a scoring system for fuel refilling stations based on water in fuel data; and displaying a recommended fuel station based on output of the scoring system. The method further comprises storing data for the refilling stations in a data structure, the data structure including data for volumes of fuel received from the fuel refilling stations. The method further comprises generating a binary search tree for searching water in fuel data for the fuel refilling stations. The method includes where the recommended fuel station is a fuel station that is determined to supply a desired level of water in fuel. The method includes where the scoring system is based on water content.

Referring now to FIG. 5, a schematic diagram illustrating how scores based on water in fuel received from fuel refilling stations may be assigned to fuel refilling stations is shown. Water content may be scored with values in a range first range 502, a second range 504, and a third range 506. Water content falling into the first range 502 may be assigned a score of +1. Water content falling into the second range 504 may be assigned a score of 0. Water content falling into the third range 506 may be assigned a score of −1. Lists of fuel refilling stations may be generated according to score as indicated at 510-514. The lists may then be applied to update the data at nodes A-E, where nodes A-E are nodes for each cataloged fuel refilling station.

As will be appreciated by one of ordinary skill in the art, the method described herein may represent one or more of any number of processing strategies such as event-driven, interrupt-driven, multi-tasking, multi-threading, and the like. As such, various steps or functions illustrated may be performed in the sequence illustrated, in parallel, or in some cases omitted. Likewise, the order of processing is not necessarily required to achieve the objects, features, and advantages described herein, but is provided for ease of illustration and description. Although not explicitly illustrated, one of ordinary skill in the art will recognize that one or more of the illustrated steps, methods, or functions may be repeatedly performed depending on the particular strategy being used.

This concludes the description. The reading of it by those skilled in the art would bring to mind many alterations and modifications without departing from the spirit and the scope of the description. For example, single cylinder, I2, I3, I4, I5, V6, V8, V10, V12 and V16 engines operating in natural gas, gasoline, diesel, or alternative fuel configurations could use the present description to advantage.

The invention claimed is:

1. A method for operating a vehicle, comprising:
via a controller, displaying to a machine/human interface a list comprised of one or more fuel refilling stations based on an indication of a content of water in fuel provided by each of the one or more fuel refilling stations based on a water in fuel sensor, where water in fuel data for each refilling station is updated based on the water in fuel sensor, where the list is generated from data stored in a data structure of the controller, the method including storing data for the refilling stations in a data structure, the data structure including data for volumes of fuel received from the fuel refilling stations, the list generated from a randomized binary search tree, the binary search tree based on a key and a priority to organize fuel refilling station data where each refilling station has a designated node in the data structure, and where the list is generated by traversing the nodes of the randomized binary search tree based on a distance between a node and a current location of the vehicle.

2. The method of claim 1, where each of the one or more fuel refilling stations is a position identified fuel refilling station, and where data stored in the data structure includes an amount of fuel determined via output of the water in fuel sensor.

3. The method of claim 1, where the indication of content of water in fuel is based on an amount of water in a reservoir.

4. The method of claim 1, further comprising generating a scoring system based on the indication of content of water in fuel and transmitting a fuel station score generated from the scoring system to a cloud server.

5. The method of claim 4, where the scoring system includes numerical values that indicate the content of water in fuel.

6. The method of claim 1, where the displaying the list includes displaying the list according to fuel refilling station scores.

7. The method of claim 6, where the fuel refilling station scores are based on the content of water in fuel.

8. A vehicle system, comprising:
a fuel tank;
a water separator including a water in fuel sensor; and
a controller including executable instructions stored in non-transitory memory that cause the controller to generate a data structure that includes data for a plurality of fuel refilling stations and data for an amount of fuel received from each of the plurality of fuel refilling stations, and instructions to update the data structure with new readings from the water in fuel sensor, and to display a list comprised of one or more fuel refilling stations based on an indication of a content of water in fuel provided by each of the one or more fuel refilling stations, the content of water in fuel provided by each of the one or more fuel refilling stations based on data included in the data structure, the list generated from a randomized binary search tree, the binary search tree based on a key and a priority to organize fuel refilling station data where each refilling station has a designated node in the data structure, and where the list is generated by traversing the nodes of the randomized binary search tree based on a distance between a node and a current location of the vehicle.

9. The vehicle system of claim 8, further comprising additional instructions to estimate the content of water in fuel according to output of a fuel level sensor and to send a fuel station score to a cloud server.

10. The vehicle system of claim 8, further comprising additional instructions to generate scores for each of the one or more fuel refilling stations, where the scores are generated according to a plurality of content of water in fuel values.

11. The vehicle system of claim 8, where the scores are based on the content of water in fuel.

12. The vehicle system of claim 8, where displaying the list includes sorting the one or more fuel refilling stations based on scores of each of the one or more fuel refilling stations.

13. The vehicle system of claim 12, where the scores of each of the one or more fuel refilling stations are based on the content of water in fuel.

14. The vehicle system of claim 13, where the content of water in fuel is based on output of the water in fuel sensor.

* * * * *